United States Patent
Block et al.

(10) Patent No.: US 11,408,888 B2
(45) Date of Patent: Aug. 9, 2022

(54) EARLY DETECTION OF HEPATOCELLULAR CARCINOMA

(71) Applicant: DREXEL UNIVERSITY, Philadelphia, PA (US)

(72) Inventors: Timothy M. Block, Doylestown, PA (US); Mengjun Wang, Mount Pleasant, SC (US); Anand Mehta, Mt. Pleasant, SC (US); Mary Ann Comunale, Bangor, PA (US)

(73) Assignee: Drexel University, Philadelphia, PA (US)

( * ) Notice: Subject to any disclaimer, the term of this patent is extended or adjusted under 35 U.S.C. 154(b) by 632 days.

(21) Appl. No.: 16/079,352

(22) PCT Filed: Feb. 16, 2017

(86) PCT No.: PCT/US2017/018040
§ 371 (c)(1),
(2) Date: Aug. 23, 2018

(87) PCT Pub. No.: WO2017/146971
PCT Pub. Date: Aug. 31, 2017

(65) Prior Publication Data
US 2019/0064171 A1 Feb. 28, 2019

Related U.S. Application Data

(60) Provisional application No. 62/300,142, filed on Feb. 26, 2016.

(51) Int. Cl.
| | | |
|---|---|---|
| *G01N 31/00* | (2006.01) | |
| *G01N 33/53* | (2006.01) | |
| *G01N 33/574* | (2006.01) | |
| *G01N 33/68* | (2006.01) | |
| *C07K 16/06* | (2006.01) | |
| *A61K 38/16* | (2006.01) | |

(52) U.S. Cl.
CPC ....... G01N 33/57438 (2013.01); A61K 38/16 (2013.01); C07K 16/06 (2013.01); G01N 33/6854 (2013.01); G01N 33/6857 (2013.01); C07K 2317/41 (2013.01)

(58) Field of Classification Search
None
See application file for complete search history.

(56) References Cited

U.S. PATENT DOCUMENTS

| | | |
|---|---|---|
| 2007/0037221 A1 | 2/2007 | Block et al. |
| 2009/0136960 A1 | 5/2009 | Lubman et al. |
| 2012/0196277 A1* | 8/2012 | Block ............ G01N 33/57438 435/5 |
| 2015/0198610 A9 | 7/2015 | Romano et al. |

FOREIGN PATENT DOCUMENTS

| | | |
|---|---|---|
| JP | 2008-541060 A | 11/2008 |
| WO | WO 2008/021163 A2 | 2/2008 |

OTHER PUBLICATIONS

Wang et al. BMC medical Genomics 2013, 6 (Suppl):S9, pp. 1-14 (Year: 2013).*
Comunale et al. (Journal of Proteome Research, vol. 5, No. 2, 2006, pp. 308-315). (Year: 2006).*
Wang et al. BMC medical Genomics 2013, 6 (Suppl):S9, pp. 1-14. 006) (Year: 2013).*
Kricka (Clinical Chemistry, vol. 45, No. 7, pp. 942-956, 1999). (Year: 1999).*
Amano et al., "Production of Functional Lectin in Pichia pastoris Directed by Cloned cDNA from Aleuria aurantia", Biosci. Biotechnol. Biochem., 2003, 67, 2277-2279.
Block et al., "Use of targeted glycoproteomics to identify serum glycoproteins that correlate with liver cancer in woodchucks and humans", Proc Natl Acad Sci, 2005, 102: 779-784.
Bouyain et al., "An Endogenous Drosophila Receptor for Glycans Bearing α1,3-Linked Core Fucose Residues", J. Biol. Chem, Jun. 21, 2002, 277, 22566-72.
Comunale et al., "Identification and development of fucosylated glycoproteins as biomarkers of primary hepatocellular carcinoma", J. Proteome Res., 2009, 8(2), 595-602.
Comunale et al., "Proteomic analysis of serum associated fucosylated glycoproteins in the development of primary hepatocellular carcinoma", Journal of Proteome Research, 2006, 6, 308-315.
Comunale et al., "Total serum glycan analysis is superior to Lectin-FLISA for the early detection of hepatocellular carcinoma", Proteomics Clin. Appl. 2013, 7, 690-700.
De Jager et al., "Improved multiplex immunoassay performance in human plasma and synovial fluid following removal of interfering heterophilic antibodies", Journal of Immunological Methods, May 2005, vol. 300, No. 1-2, 124-135.
Drake et al., "Lectin Capture Strategies Combined with Mass Spectrometry for the Discovery of Serum Glycoprotein Biomarkers", Mol Cell Proteomics. 2006; 5; 1957-6.

(Continued)

*Primary Examiner* — Lisa V Cook
(74) *Attorney, Agent, or Firm* — BakerHostetler

(57) ABSTRACT

Provided are methods, assays, and kits for detecting hepatocellular carcinoma, as well as methods for stratifying subjects among higher and lower risk categories for having hepatocellular carcinoma, and methods of treating and managing treatment of subjects that are suspected or at risk of having hepatocellular carcinoma. Although previous work has attempted to address the need for a highly sensitive, early predictor of hepatocellular carcinoma by assessment of one or more biological factors, none have approached the degree of sensitivity that is required for clinically relevant determination of whether a subject, especially a non-symptomatic subject, has that condition. The present inventors have discovered that certain combinations of factors fulfill this need by conferring a high level of accuracy that was not previously attainable.

16 Claims, 2 Drawing Sheets

(56) References Cited

OTHER PUBLICATIONS

Drickamer, "C-type lectin-like domains", Curr. Opin. Struct. Biol., 1999, 9(5), 585-589.
Elnaggar et al., "Clinical Value of Fetuin A in Cirrhosis Associated Hepatocellular Carcinoma", Medical Journal of Cairo University, Dec. 2014, vol. 82, No. 1, 725-730.
Hyoung-Joo Lee et al., "Simple Method for Quantitative Analysis of N-Linked Glycoproteins in Hepatocellular Carcinoma Specimens", Journal of Proteome Research, Jan. 2010, vol. 9, No. 4, 308-318.
Ishida et al., "Molecular Cloning and Overexpression of fleA Gene Encoding a Fucose-specific Lectin of *Aspergillus oryzae*", Biosci. Biotechnol. Biochem., 2002, 66(5), 1002-8.
Kohler and Milstein, "Continuous cultures of fused cells secreting antibody of predefined specificity", Nature, Aug. 7, 1975, 256, 495-497.
Kricka, "Human Anti-Animal Antibody Interferences in Immunological Assays", Clinical Chemistry, Apr. 15, 1999, vol. 45, No. 7, 942-56.
Loris et al., "Structural Basis of Carbohydrate Recognition by the Lectin LecB from *Pseudomonas aeruginosa*", J. Mol. Biol., Aug. 2003, 331, 861-867.
Mansour et al., "Distinct binding patterns of fucose-specific lectins from *Biomphalaria alexandrina* and *Lotus tetragonolobus* to murine lymphocyte subsets", Immunobiology, 2005, 210, 335-348.
Mehta et al., "Increased Levels of Galactose-Deficient Anti-Gal Immunoglobulin G in the Sera of Hepatitis C Virus-Infected Individuals with Fibrosis and Cirrhosis", J Virol., 2008, 82, 1259-1270.
Mengjun Wang et al., "Biomarker analysis of fucosylated kininogen through depletion of lectin reactive heterophilic antibodies in hepatocellular carcinoma", Journal of Immunological Methods, Nov. 2018, vol. 462, 59-64.
Naitoh et al., "Highly enhanced fucosylation of serum glycoproteins in patients with hepatocellular carcinoma", J Gastroenterol Hepatol, 1999, 14: 436-445.
Roy et al., "Detection of Root Mucilage Using an Anti-fucose Antibody", Ann. Bot., 2002, 89, 293-299.
Srikrishna et al., "Fucose$\beta$-1-P-Ser is a new type of glycosylation: using antibodies to identify a novel structure in *Dictyostelium discoideum* and study multiple types of fucosylation during growth and development", Glycobiology, Aug. 1998, 8(8), 799-811.
Steel et al., "Efficient and Specific Removal of Albumin from Human Serum Samples", Molecular & Cellular Proteomics, American Society for Biochemistry and Molecular Biology, Jan. 2003, vol. 2, No. 4, 262-270.
Wang et al., "A comparison of statistical methods for the detection of hepatocellular carcinoma based on serum biomarkers and clinical variables", BMC Medical Genomics, Nov. 11, 2013, 6(Suppl 3), S9.
Wang et al., "Novel Fucosylated Biomarkers for the Early Detection of Hepatocellular Carcinoma", Cancer Epidemiol Biomarkers Prev., Jun. 2009, 18(6), 1914-1921.
Wong et al., "Can we use HCC risk scores to individualize surveillance in chronic hepatitis B infection?", Journal of Hepatology, May 2015, vol. 63, No. 3, 722-732.
(GE Healthcare) Antibody Purification. Product handbook [online]. Feb. 2015 [retrieved on Apr. 15, 2017]. Retrieved from the Internet: <URL: https://proteins.gelifesciences.com/~/media/protein-purification-ib/documents/handbooks/antibody_purification_handbook.pdf?la=en> p. 52, 2nd paragraph; p. 111, 1st paragraph; Table 1.1 b; Table 3.1.
Wang Mengjun et al: "Identification of IgM as a contaminant in lectin-FLISA assays for HCC detection", Biochemical and Biophysical Research Communications, Elsevier, Amsterdam, NL, vol. 476, No. 3, May 13, 2016 (May 13, 2016), pp. 140-145.

* cited by examiner

EARLY DETECTION OF HEPATOCELLULAR CARCINOMA

CROSS-REFERENCE TO RELATED APPLICATIONS

This application is the National Stage Application of International Patent Application No. PCT/US2017/018040, filed Feb. 16, 2017, which claims the benefit of priority to U.S. Provisional Application No. 62/300,142, filed Feb. 26, 2016, the entire contents of both of which are incorporated herein by reference.

CROSS-REFERENCE TO RELATED APPLICATIONS

This application claims the benefit of priority to U.S. Provisional Application No. 62/300,142, filed Feb. 26, 2016, the entire contents of which are incorporated herein by reference.

TECHNICAL FIELD

The present disclosure concerns assays, kits, and methods for the detection of liver disease, patient stratification, and therapeutic intervention.

BACKGROUND

Infection with hepatitis B virus (HBV) and/or hepatitis C virus (HCV) is the major etiology of hepatocellular cancer (HCC). Both HBV and HCV cause acute and chronic liver infections and most chronically infected individuals remain asymptomatic for many years as clinical disease (HCC and cirrhosis) usually requires decades to develop. Ten to forty percent of all chronic HBV carriers eventually develop liver cancer, and it is estimated that over one million people worldwide die because of HBV/HCV associated liver cancer. Indeed, HBV and HCV infections are associated with over 80% of all HCC cases worldwide and can be as high as 96% in regions where HBV is endemic.

The progression of liver disease into liver cancer is monitored primarily by the use of serum levels of the oncofetal glycoprotein, alpha-fetoprotein (AFP) or the core fucosylated glycoform of AFP (AFP-L3). However, AFP can be produced under many circumstances, including other liver diseases, such as human hepatoma, hepatoblastoma, and hepatitis B infection, and is not present in all those with HCC. Hence, the use of AFP as a primary screen for HCC has been questioned and a need exists for more sensitive serum biomarkers for HCC.

The glycosylation of proteins can be cell-specific, and the N-linked glycan that a protein carries is a modification that occurs in the cell from which it came. Sugar (glycan) structures on a protein that is secreted from malignant or diseased tissue may, and often do, differ from the glycans that are present on the same protein from normal cells. Indeed, numerous studies have observed changes in N-linked glycosylation with the development of cirrhosis and hepatocellular carcinoma (HCC) (see, e.g., Naitoh, A., et al., Highly enhanced fucosylation of serum glycoproteins in patients with hepatocellular carcinoma. J Gastroenterol Hepatol, 14: 436-445, 1999; Block, T. M., et al., Use of targeted glycoproteomics to identify serum glycoproteins that correlate with liver cancer in woodchucks and humans. Proc Natl Acad Sci USA, 102: 779-784, 2005). For example, in individuals chronically infected with HCV and having a diagnosis of HCC, the amount of fucosylated N-linked glycan derived from total protein preparations isolated from serum was consistently greater than that of healthy subjects or those with HCV and "inactive" disease (Comunale, M. A., et al., Proteomic analysis of serum associated fucosylated glycoproteins in the development of primary hepatocellular carcinoma. Journal of Proteome Research., 6: 308-315, 2006).

However, it has not yet been possible to identify a single glycoprotein, glycosylation pattern, biomarker suite, or other indicator of HCC that confers a high degree of sensitivity and ability for early detection. There remains an outstanding need for early detectors of HCC.

SUMMARY

Provided herein are methods for detecting hepatocellular carcinoma in a subject comprising removing IgG and IgM proteins from a biological fluid from the subject; measuring the amount of one or more biomarkers in the biological fluid; determining the age and gender of the subject; and, determining the absence or presence of hepatocellular carcinoma in the subject using an optimized output of a function of the determined age and gender, and the measured biomarkers in the biological fluid.

The identities of individual biomarkers that are measured in accordance with the present disclosure are both specific and critical to the accuracy of the detection of hepatocellular carcinoma, but for the sake of brevity, the inventive combinations of biomarkers are omitted from the present summary.

Also disclosed are assays for detecting hepatocellular carcinoma in a subject comprising measuring the amount of one or more biomarkers in the biological fluid, wherein the assay utilizes reagents for removing IgG and IgM proteins from a biological fluid of the subject prior to the measuring steps; determining the age and gender of the subject; and, determining the absence or presence of hepatocellular carcinoma in the subject using an optimized output of a function of the determined age and gender, and the measured biomarkers in the biological fluid.

The present disclosure also pertains to kits for detecting hepatocellular carcinoma in a subject comprising a reagent for removing IgG protein from a biological fluid, and a reagent for removing IgM protein from a biological fluid from the subject; reagents for respectively measuring one or more biomarkers in the biological fluid; and, instructions for determining the absence or presence of hepatocellular carcinoma in the subject using an optimized output of a function of the determined age and gender, and the measured biomarkers in the biological fluid.

Also provided herein are methods for assigning a subject to a group having a higher or lower probability of hepatocellular carcinoma comprising removing IgG and IgM proteins from a biological fluid from the subject; measuring the amount of one or more biomarkers in the biological fluid; determining the age and gender of the subject; and, assigning the subject to a group having a higher or lower probability of hepatocellular carcinoma based on an optimized output of a function of the determined age and gender, and the measured biomarkers in the biological fluid.

The present disclosure also provides methods for managing treatment of a subject suspected of having hepatocellular carcinoma comprising removing IgG and IgM proteins from a biological fluid from the subject; measuring the amount of one or more biomarkers in the biological fluid; determining the age and gender of the subject; and, treating the subject based on an optimized output of a function of the determined age and gender, and the measured biomarkers in the biological fluid, wherein the subject is treated for hepatocellular carcinoma when the subject is determined to have that disease based on the output of the function.

BRIEF DESCRIPTION OF THE DRAWINGS

FIG. 1A summarizes the AUROC data for the discrimination of all patients with HCC (N=115) from all patients with cirrhosis (N=93); with early-stage HCC (N=69) from cirrhosis (N=93); with AFP negative (AFP−, having a level of AFP within the range that is observed among normal subjects, e.g., without HCC) HCC (N=39) from AFP negative cirrhosis (N=84); and with both early-stage and AFP negative HCC (N=29) from AFP negative cirrhosis (N=84). FIG. 1B summarizes the sensitivity values at 90% specificity cutoffs for discrimination of the same respective patient groups in the same study, and FIG. 1C summarizes the sensitivity values at 95% specificity cutoffs for discrimination of the same respective patient groups in the same study.

DETAILED DESCRIPTION OF ILLUSTRATIVE EMBODIMENTS

Figure 1A:
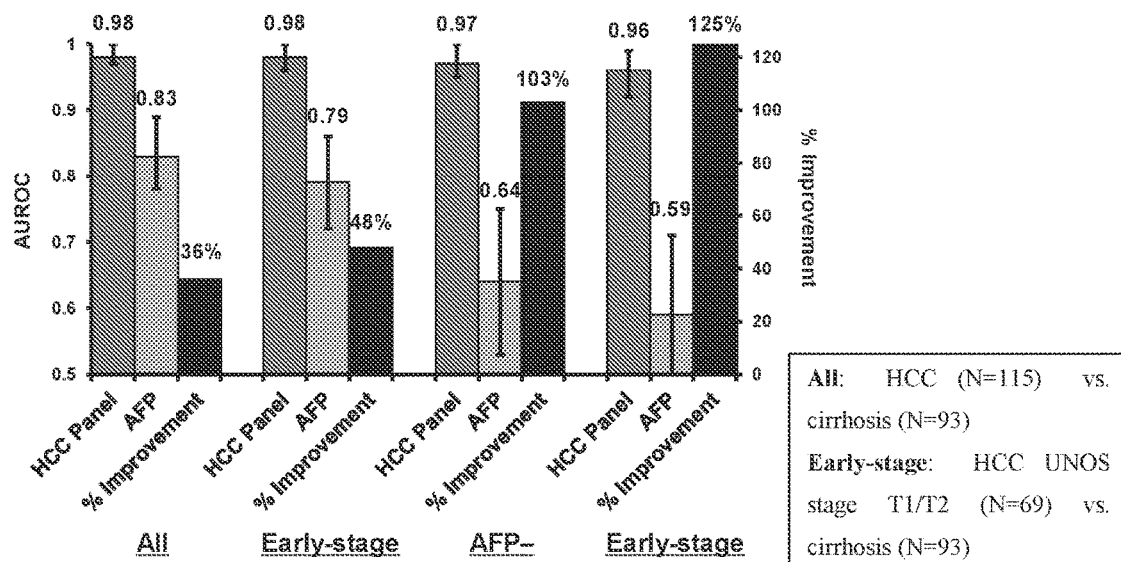
FIGS. 1A-1C depict the results of an evaluation of a panel consisting of fucosylated low molecular weight kininogen, alpha-fetoprotein, aspartate aminotransferase (AST), alkaline phosphatase (ALK), age, and gender.

The present inventions may be understood more readily by reference to the following detailed description taken in connection with the accompanying figures and examples, which form a part of this disclosure. It is to be understood that these inventions are not limited to the specific methods, assays, kits, conditions, or parameters described and/or shown herein, and that the terminology used herein is for the purpose of describing particular embodiments by way of example only and is not intended to be limiting of the claimed inventions.

The entire disclosures of each patent, patent application, and publication cited or described in this document are hereby incorporated herein by reference.

As employed above and throughout the disclosure, the following terms and abbreviations, unless otherwise indicated, shall be understood to have the following meanings.

In the present disclosure the singular forms "a," "an," and "the" include the plural reference, and reference to a particular numerical value includes at least that particular value, unless the context clearly indicates otherwise. Thus, for example, a reference to "a reagent" is a reference to one or more of such reagents and equivalents thereof known to those skilled in the art, and so forth. Furthermore, when indicating that a certain element "may be" X, Y, or Z, it is not intended by such usage to exclude in all instances other choices for the element.

When values are expressed as approximations, by use of the antecedent "about," it will be understood that the particular value forms another embodiment. As used herein, "about X" (where X is a numerical value) preferably refers to ±10% of the recited value, inclusive. For example, the phrase "about 8" can refer to a value of 7.2 to 8.8, inclusive; as another example, the phrase "about 8%" can refer to a value of 7.2% to 8.8%, inclusive. Where present, all ranges are inclusive and combinable. For example, when a range of "1 to 5" is recited, the recited range should be construed as optionally including ranges "1 to 4", "1 to 3", "1-2", "1-2 & 4-5", "1-3 & 5", and the like. In addition, when a list of alternatives is positively provided, such a listing can also include embodiments where any of the alternatives may be excluded. For example, when a range of "1 to 5" is described, such a description can support situations whereby any of 1, 2, 3, 4, or 5 are excluded; thus, a recitation of "1 to 5" may support "1 and 3-5, but not 2", or simply "wherein 2 is not included."

As used herein, the terms "treatment" or "therapy" (as well as different word forms thereof) includes preventative (e.g., prophylactic), curative, palliative, or anti-proliferative treatment. Such preventative, curative, palliative, or anti-proliferative treatment may be full or partial. For example, complete elimination of unwanted symptoms, or partial elimination of one or more unwanted symptoms would represent "treatment" as contemplated herein.

The present disclosure relates to, among other things, methods, assays, and kits for detecting hepatocellular carcinoma, as well as methods for stratifying subjects among higher and lower risk categories for having hepatocellular carcinoma, and methods of treating and managing treatment of subjects that are suspected or at risk of having hepatocellular carcinoma. Unless otherwise specified, the steps, reagents, and factors (such as biomarkers) that are disclosed with respect to one aspect of the present disclosure (such as in connection with any of the present methods, kits, and assays) may be employed in connection with any other aspect of this disclosure.

Although previous work has attempted to address the need for a highly sensitive, early predictor of hepatocellular carcinoma by assessment of one or more biological factors, none have approached the degree of sensitivity that is required for clinically relevant determination of whether a subject, especially a non-symptomatic subject, has that condition. The present inventors have discovered that certain combinations of factors fulfill this need by conferring a high level of accuracy that was not previously attainable. Importantly, the identified combinations can utilize factors that, on an individual basis, have not represented accurate detectors of hepatocellular carcinoma, can omit factors that have traditionally been thought to represent indicators of the disease, or both. These and other features of the presently disclosed subject matter are described more fully herein.

Provided herein are methods for detecting hepatocellular carcinoma in a subject or determining the likelihood that a subject has hepatocellular carcinoma comprising removing IgG and IgM proteins from a biological fluid from the subject; measuring the amount of one or more biomarkers in the biological fluid; determining the age and gender of the subject; and, determining the absence or presence of hepatocellular carcinoma in the subject using an optimized output of a function of the determined age and gender, and the measured biomarkers in the biological fluid.

During the course of discovery of the presently disclosed subject matter, the inventors observed that it was not possible to identify certain glycoforms, including fucose-containing glycoforms, of proteins within a biological fluid from a subject. The inventors determined that some material was present in subject samples that produced a non-specific signal in the assays that were used for identifying glycoforms, and ultimately discovered that a primary confounding material was IgM. It was further discovered that removal of both IgM and IgG removed the contaminating signal and permitted accurate analysis of specific protein glycoforms in a manner that was not previously possible. The steps of removing IgM and also IgG and the reagents for accomplishing these steps have surprisingly been determined to represent clinically essential aspects of the process of early detection of hepatocellular carcinoma according to the present methods, assays, and kits. In some embodiments, the IgG is removed by incubating the biological fluid with Protein A/G, which was found to be more effective than other tested strategies, and the IgM is removed by passing the biological fluid through a filter. The filter may be, for example, a 1000 kD filter, a 900 kD filter, a 800 kD filter, a 500 kD filter, a 450 kD filter, a 400 kD filter, a 350 kD filter, a 300 kD filter, a 250 kD filter, a 200 kD filter, a 175 kD filter, a 150 kD filter, a 125 kD filter, a 100 kD filter, an 80 kD filter, a 75 kD filter, a 70 kD filter, a 60 kD filter, a 50 kD filter, a 40 kD filter, a 30 kD filter, a 25 kD filter, a 20 kD filter, a 15 kD filter, or a 10 kD filter. Filtration may accomplished, for example, by gravity or centrifugation. Alternatively, the IgG and IgM may both be removed by precipitation using polyethylene glycol. In accordance with such embodiments, the serum may be incubated with polyethylene glycol and then subjected to centrifugation, with the resulting supernatant representing the material in which the respective amounts of biomarkers of interest are measured.

Any biological fluid may be used pursuant to the present invention. For example, the biological fluid may be whole blood, serum, plasma, urine, saliva, tears, mucous, or a combination of two or more of these fluids.

Following removal of IgG and IgM from the biological fluid, the amount of one or more biomarkers in the biological fluid is measured. The "amount" of a biomarker in the biological fluid may refer to its concentration in the biological fluid, for example, as expressed in terms of ng/mL, or, in the case of a biomarker being a fucosylated glycoprotein, may refer to the quantity of the biomarker in the biological sample that is fucosylated relative to the quantity of the biomarker in the sample that is not fucosylated. In some embodiments, the amount of the fucosylated biomarker may be expressed in terms of a percentage relative to the total amount of biomarker in the sample.

Previous work has identified more than 50 glycoproteins that exhibit increased fucosylation in subjects known to have hepatocellular carcinoma, cirrhosis, or both (Comunale, M. A., et al. J Proteome Res. 2006 February;5(2):308-15). Various published studies have assessed the ability of individual fucosylated glycoproteins to function as markers for hepatocullar carcinoma, including fetuin A (also called alpha-2-HS-glycoprotein) (Comunale, Mass., et al. J. Proteome Res. 2009; 8; 595-602), kininogen (Wang, M, et al. J Cancer Epidemiol Biomarkers Prev. 2009; 18; 1914-1921), alpha-1 antitrypsin (id.), hemopexin (Comunale, Mass., et al. 2009), alpha-1-antichymotrypsin (Comunale, M A, et al. Proteomics Clin. Appl. 2013; 7; 690-700), GP73 (Drake, R R, et al. Mol Cell Proteomics. 2006; 5; 1957-67), and LRAGG (lectin-reactive anti-α-galactose IgG) (Mehta, A S, et al. J Virol. 2008; 82; 1259-1270). Among these glycoproteins, top performers included, for example, hemopexin (AUROC=0.87) and fetuin-A (AUROC=0.90). The present inventors have determined that certain combinations of factors (which may be referred to as panels), some of which factors are fucosylated glycoproteins, can be used to identify the presence of hepatocellular carcinoma with considerably more accuracy than by assessment of any individual glycoprotein or other individual factor. Unexpectedly, certain glycoproteins that functioned as the best indicators of hepatocellular carcinoma when assessed individually had only a moderate contribution, or even a negative contribution to panels of factors (such as one or more other fucosylated glycoproteins) that included assessment of such proteins, among others. Accordingly, it was found that previous work identifying individual indicators of hepatocellular carcinoma could not be used to predict the contribution of those indicators to a panel of factors for the identification of subjects having hepatocellular carcinoma.

In accordance with the present methods, the biomarkers whose respective amounts are measured may be one or more of alkaline phosphatase, GP-73, hemopexin, HBsAg, hepatitis B viral particle, alpha-acid-glycoprotein, alpha-1-antichymotrypsin, alpha-1-antichymotrypsin His-Pro-less, alpha-1-antitrypsin, serotransferrin, ceruloplasmin, alpha-2-macroglobulin, fetuin-A/alpha-2-HS-glycoprotein, alpha-fetoprotein, haptoglobin, Fibrinogen gamma chain precursor, immunoglobulin (including, for example, IgA, IgD, IgE), APO-D, kininogen, histidine rich glycoprotein, Complement factor 1 precursor, complement factor I heavy chain, complement factor I light chain, Complement C1s, Complement factor B precursor, complement factor B Ba fragment, Complement factor B Bb fragment, Complement C3 precursor, Complement C3 beta chain, Complement C3 alpha chain, C3a anaphylatoxin, Complement, C3b alpha' chain, Complement C3c fragment, Complement C3dg fragment, Complement C3g fragment, Complement C3d fragment, Complement C3f fragment, Complement C5, Complement C5 beta chain, Complement C5 alpha chain, C5a anaphylatoxin, Complement C5 alpha' chain, Complement C7, B-2-glycoprotein, Vitamin D-binding protein, Inter-alpha-trypsin inhibitor heavy chain H2, alpha-1B-glycoprotein, Angiotensinogen precursor, Angiotensin-1, Angiotensin-2, Angiotensin-3, GARP protein, beta-2-glycoprotein, Clusterin (Apo J), Integrin alpha-8 precursor glycoprotein, Integrin alpha-8 heavy chain, Integrin alpha-8 light chain, hepatitis C viral particle, elf-5, kininogen, HSP33-homolog, lysyl endopeptidase, and Leucinerich repeat-containing protein 32 precursor. In some embodiments, a glycoform of these glycoproteins is measured in accordance with the present methods. For example, N-linked glycosylated forms of these glycoproteins may be measured, such as the fucosylated N-linked glycoform of the biomarker, and, in particular, the core-fucosylated N-linked glycoform may be measured. Additional biomarkers can be one or more of alanine aminotransferase, aspartate aminotransferase, bilirubin, albumin, platelet count, or white blood cell count. In addition, change over time in the amount of any of the above-referenced factors can represent a "biomarker" in accordance with the present disclosure.

In certain embodiments, the biomarkers whose respective amounts are measured are one or more of alpha-fetoprotein, fucosylated fetuin-A, fucosylated hemopexin, fucosylated kininogen, fucosylated alpha-1-antitrypsin, aspartate aminotransferase (AST), alanine aminotransferase (ALT), and alkaline phosphatase (ALK). In one aspect, the present methods comprise measuring alpha-fetoprotein, fucosylated kininogen, ALK, and AST. In another aspect, the present methods comprise measuring alpha-fetoprotein, fucosylated kininogen, ALK, AST, and fucosylated alpha-1-antitrypsin. In a further aspect, the present methods comprise measuring alpha-fetoprotein, fucosylated kininogen, ALK, AST, and fucosylated fetuin-A. The present methods may alternatively comprise measuring alpha-fetoprotein, fucosylated kininogen, ALK, AST, fucosylated fetuin-A, and fucosylated alpha-1-antitrypsin. Other combinations of biomarkers that are measured in accordance with the present methods include: alpha-fetoprotein and fucosylated fetuin-A; alpha-fetoprotein and fucosylated hemopexin; alpha-fetoprotein and fucosylated kininogen; alpha-fetoprotein, fucosylated fetuin-A, and fuoxylated hemopexin; alpha-fetoprotein, fucosylated fetuin-A, and fucosylated kininogen; alpha-fetoprotein, fucosylated alpha-1 antitrypsin, and fucosylated kininogen; and, alpha-fetoprotein, fucosylated alpha-1 antitrypsin, fucosylated fetuin A, and fucosylated kininogen.

Any acceptable process for determining the respective amounts of the biomarkers may be used in accordance with the present methods. Total protein biomarkers, such as total alpha-fetoprotein, may be detected using conventional techniques, such as an immunoassay. When the biomarker is glycosylated, a detection reagent can directly label the glycosyl moieties, for example, via carbohydrate specific chemicals or dyes, or via labeled lectins, labeled carbohydrate binding proteins, or labeled antibodies. The detection reagent can be a secondary reagent, for example, by first capturing the target analyte and then contacting the capture reagent-target complex with a labeled secondary reagent. In some embodiments, detection and quantification can proceed by separating glycosyl moieties from the proteins prior to the quantifiable detection of glycosylation. In other embodiments, the glycoproteins can be separated from the biological fluid prior to the quantifiable detection of glycosylation. These approaches and others are described in U.S. Pub. No. 2012/0196277, filed Apr. 10, 2012, the entire contents of which are incorporated herein by reference. When a lectin is used to detect a glycosylated protein, the lectin may be wild-type, or may be a recombinant lectin that possesses enhanced binding affinity for a particular glycan of interest. For example, U.S. Pub. No. 2015/0198610, filed Feb. 3, 2012, which is incorporated herein by reference, discloses various recombinant Aleuria aurantia lectins that are characterized by enhanced binding to core fucosyl moieties, which are known to be present to a greater degree on glycoproteins of subjects having hepatocellular carcinoma, as compared with glycoproteins of subjects that do not have the disease.

The respective amounts of ALT and AST may be determined using a kinetic assay based on the respective enzymatic activities of AST and ALT using colorimetric, spectrophotometric, chemiluminescence, chromatography, fluorescence or UV absorbance, radiochemical, and electrochemical techniques for detection. Those of ordinary skill in the art are familiar with such assays and techniques.

Pursuant to the present methods, the age and gender of the subject are determined. The age of the subject may be expressed in terms of years, months, or days, as desired. Age and gender have previously been shown to represent relevant factors among subjects with hepatocellular carcinoma (see Wang, M., et al., Proceedings. IEEE International Conference on Bioinformatics and Biomedicine 2012; Wang, M., et al., BMC Medical Genomics, 2013, 6 Suppl 3: S9).

Following measurement of the respective amounts of specific biomarkers and determination of the age and gender of the subject, the absence or presence of hepatocellular carcinoma is determined using an optimized output of a function of the determined age and gender, and the respective measured amounts of the biomarkers. For example, the function may comprise respective optimized weighting coefficients for the determined age and gender, and for the measured amounts of biomarker. Appropriate statistical methodologies may be used for identifying an optimized function of the age, gender, and biomarker amounts. For example, one may use logistic regression with respect to each desired panel of factors (i.e., biomarkers, age, and gender), in order to generate logistic regression algorithms. To judge the fitness of each regression, one may derive one or more of AIC, $R^2$, Dxy, Likelihood ratio test, Pearson's goodness-of-fit, Log-likelihood, Deviation statistic, Tau-a, NRI, and the area under ROC curve (AUC) of apparent validation (see Steyerberg, E. (2009), "Clinical Prediction Models", Springer-Verlag New York). From these criteria and tests, one may select logistic regression models that had the highest fitness for further evaluation. Optionally, to avoid over-fitting, one may apply one or more of leave-one-out cross-validation, bootstrap-validation, and 3-fold cross-validation in order to validate the candidate models.

The optimized function of the age, gender, and biomarker amounts yield a value expressing the probability that the subject has hepatocellular carcinoma. In accordance with the present methods, the value may reveal that the subject has hepatocellular carcinoma at clinically relevant level of certainty. For example, the level of certainty may be about 50% or higher, 60% or higher, 70% or higher, 75% or higher, 80% or higher, 85% or higher, 90% or higher, about 91% or higher, about 92% or higher, about 93% or higher, about 94% or higher, about 95% or higher, about 96% or higher, about 97% or higher, or about 98% or higher. Accordingly, the present methods can be used to determine whether a subject has hepatocellular carcinoma with a very high degree of certainty.

As used herein, "detecting hepatocellular carcinoma" or "determining the absence or presence of hepatocellular carcinoma" can embrace the detection of hepatocellular carcinoma in a subject that is of a type or a stage that is not typically detectable by methods already existing at the time of the present disclosure. For example, the presently disclosed methods, assays, and kits can be used to determine if a subject has early stage hepatocellular carcinoma; alpha fetoprotein negative (AFP$^-$) hepatocellular carcinoma; or, early stage hepatocellular carcinoma and alpha fetoprotein negative (AFP$^-$) hepatocellular carcinoma (i.e., HCC that is both early stage and AFP).

"Alpha fetoprotein negative (AFP$^-$) hepatocellular carcinoma" refers to disease that is not characterized by levels of AFP that vary significantly from AFP levels found in subjects without liver disease. For example, when the amount of AFP in a biological sample from a subject is less than about 20 ng/mL, then the subject can be said to be AFP$^-$.

Significantly, the data provided in the present disclosure, for example, in Tables 3A and 3B, demonstrates the ability of the presently disclosed methods, assays, and kits to provide a system whereby an early-stage and/or alpha fetoprotein negative hepatocellular carcinoma can be detected in a subject. Appropriate treatment can follow. The high degree of clinical significance of this aspect of the inventive subject matter will be apparent to those of ordinary skill in the art, especially given that early stage hepatocellular carcinoma is curable (whereas later-stage disease is typically eligible only for palliative care). Unlike the presently disclosed subject matter, previous systems for detecting hepatocellular carcinoma have been unable to detect early stage hepatocellular carcinoma, alpha fetoprotein negative (AFP$^-$) hepatocellular carcinoma, or early stage hepatocellular carcinoma and alpha fetoprotein negative (AFP$^-$) hepatocellular carcinoma.

Thus, the present disclosure also provides methods that include treating or recommending treatment of a subject specifically for early stage hepatocellular carcinoma, alpha fetoprotein negative hepatocellular carcinoma, or early stage hepatocellular carcinoma that is also alpha fetoprotein negative hepatocellular carcinoma. Such methods may be adjunct to the presently disclosed methods for detecting hepatocellular carcinoma, or may be an outcome of the use of the presently disclosed assays and kits. Appropriate treatments that are tailored specifically for early stage hepatocellular carcinoma, alpha fetoprotein negative hepatocellular carcinoma, or early stage hepatocellular carcinoma that is also alpha fetoprotein negative hepatocellular carcinoma can be identified by medical practitioners.

An exemplary method may comprise removing IgG and IgM proteins from a biological fluid from a subject suspected of having early stage hepatocellular carcinoma, AFP negative hepatocellular carcinoma, or both; measuring the amount of one or more biomarkers in the biological fluid; determining the age and gender of the subject; determining the absence or presence of early stage hepatocellular carcinoma, AFP negative hepatocellular carcinoma, or both in the subject using an optimized output of a function of the determined age and gender, and the measured biomarkers in the biological fluid; and, treating the subject or providing a recommendation of treatment of the subject in the event that early stage hepatocellular carcinoma, AFP negative hepatocellular carcinoma, or both is determined to be present in the subject, wherein the treatment is specifically selected for treatment of early stage hepatocellular carcinoma, AFP negative hepatocellular carcinoma, or both. The aspects of such methods concerning removing IgG and IgM proteins from the biological fluid, measuring the amount of one or more biomarkers in the biological fluid, determining the age and gender of the subject, and determining the absence or presence of disease using an optimized output of a function of the determined age and gender, and the measured biomarkers in the biological fluid may be performed in accordance with the corresponding aspects of the previously disclosed methods for detecting the absence or presence of hepatocellular carcinoma.

Also disclosed are assays for detecting hepatocellular carcinoma in a subject comprising measuring the amount of one or more biomarkers in the biological fluid, wherein the assay utilizes reagents for removing IgG and IgM proteins from a biological fluid of the subject prior to the measuring steps; determining the age and gender of the subject; and, determining the absence or presence of hepatocellular carcinoma in the subject using an optimized output of a function of the determined age and gender, and the measured biomarkers in the biological fluid.

The reagent for removing IgG from a biological fluid may be Protein A/G. In other embodiments, the reagent may be Protein L. As used herein with respect to the presently disclosed assays, methods, and kits, the "reagent" for removing IgM may be an article of laboratory equipment or a mechanical system. For example, the reagent for removing IgM may be a molecular-weight based filter or a filtration system. The filtration may be performed by gravity- or centrifugal-based filtration, for example. In other embodiments, the reagent for removing both IgG and IgM may be polyethylene glycol, nonlimiting examples of which include PEG-400, PEG-3350, PEG-4000, PEG-6000, and PEG-8000.

Any of a variety of different assay formats can be used pursuant to the inventive assays, in order to quantitatively detect the one or more biomarkers. Immunoassays are one preferred assay, and include but are not limited to ELISA, radioimmunoassays, competition assays, Western blotting, bead agglomeration assays, lateral flow immunoassays, immunochromatographic test strips, dipsticks, migratory format immunoassays, and the like. Other suitable immunoassays will be known to those of relevant skill in the art. Microscopy can also be used. In some embodiments, chromatography represents the chosen assay format. High performance liquid chromatography (HPLC) is particularly preferred. In some embodiments, mass spectroscopy is the preferred assay. In some embodiments, gel electrophoresis coupled with densitometry is used as the assay format.

The general format of the assays may involve contacting an appropriate reagent with a test sample containing the analytes of interest, namely the biomarkers, which may be distinguished from other components found in the sample. The sample may be the biological fluid from the subject, or may be a separate sample that was derived from the biological fluid. Following interaction of the analyte with the reagent, the system can be washed and then directly detected or detected by means of a secondary reagent.

In some embodiments, a reagent for detecting the biomarker is immobilized on a solid support. In other preferred embodiments, the test sample, or molecules separated or purified from the test sample, such as post-translationally modified polypeptides, are immobilized on a solid support. Techniques for purification of biomolecules from samples such as cells, tissues, or biological fluid are well known in the art. The technique chosen may vary with the tissue or sample being examined, but it is well within the skill of the art to match the appropriate purification procedure with the test sample source.

Examples of suitable solid supports include, but are not limited to, glass, plastic, metal, latex, rubber, ceramic, polymers such as polypropylene, polyvinylidene difluoride, polyethylene, polystyrene, and polyacrylamide, dextran, cellulose, nitrocellulose, pvdf, nylon, amylase, and the like. A solid support can be flat, concave, or convex, spherical, cylindrical, and the like, and can be particles, beads, membranes, strands, precipitates, gels, sheets, containers, wells, capillaries, films, plates, slides, and the like. The solid support can be magnetic, or a column.

The other aspects of the present assays, including the steps of measuring the amount of one or more biomarkers in the biological fluid, determining the age and gender of the subject; and, determining the absence or presence of hepatocellular carcinoma in the subject using an optimized output of a function of the determined age and gender, and the measured biomarkers in the biological fluid, may be in accordance with any of the aspects described above for the inventive methods for detecting hepatocellular carcinoma in a subject.

The present disclosure also pertains to kits for detecting hepatocellular carcinoma in a subject comprising a reagent for removing IgG protein from a biological fluid of the subject, and a reagent for removing IgM proteins from the biological fluid; reagents for respectively measuring one or more biomarkers in the biological fluid; and, instructions for determining the absence or presence of hepatocellular carcinoma in the subject using an optimized output of a function of the determined age and gender, and the measured biomarkers in the biological fluid.

The reagent for removing IgG from a biological fluid may be Protein A/G. In other embodiments, the reagent may be Protein L. The reagent for removing IgM from the biological fluid may be a molecular-weight based filter, such as a a 1000 kD filter, a 900 kD filter, a 800 kD filter, a 500 kD filter, a 450 kD filter, a 400 kD filter, a 350 kD filter, a 300 kD filter, a 250 kD filter, a 200 kD filter, a 175 kD filter, a 150 kD filter, a 125 kD filter, a 100 kD filter, an 80 kD filter, a 75 kD filter, a 70 kD filter, a 60 kD filter, a 50 kD filter, a 40 kD filter, a 30 kD filter, a 25 kD filter, a 20 kD filter, a 15 kD filter, or a 10 kD filter. Filtration may accomplished, for example, by gravity or centrifugation.

In certain embodiments, the reagent for removing IgG and the reagent for removing IgM may be the same. An exemplary embodiment of this kind is polyethylene glycol.

When a biomarker is a polypeptide, for example, a glycoprotein, the reagent for measuring the one or more biomarkers in the biological fluid may exploit the fact that the polypeptide contains one or more post-translational modifications (such as glycosylation). Detection of a post-translational modification can be accomplished by detecting a certain polypeptide-moiety complex. In another preferred embodiment, detection of the post-translational modification can be carried out by separating the polypeptide and moiety, and detecting the moiety. Detection of the polypeptide-moiety complex can be carried out using a reagent that specifically recognizes the moiety, the particular class of moiety, or the moiety as a complex with the polypeptide. Suitable detection reagents will be apparent to those of skill in the art, non-limiting examples of which are described below. The reagent can comprise multiple molecules each having specificity for a different target moiety, thereby resulting in multiple reagent-target interactions.

The reagent that is used to detect the biomarker may be an antibody. For example, any antibody that specifically binds to a target moiety of interest can be used in accordance with the present kits. Monoclonal and/or polyclonal antibodies can be used, from whatever source produced, as can recombinant antibodies such as single chain antibodies and phage-displayed antibodies, as well as chimeric and humanized antibodies. Antigen binding fragments of antibodies such as the Fab or Fv can also be used.

In some embodiments, the reagent for detecting the biomarker is an antibody that specifically recognizes glycoproteins. Preferably, the antibodies specifically recognize carbohydrate moieties, including mono- and poly-saccharides. In some instances, the antibodies specifically recognize fucose moieties, such as core fucosyl moieties. Antibodies capable of specifically recognizing fucose have been described. See, e.g., Roy S S et al. (2002) Ann. Bot. 89:293-9; and, Srikrishna G et al. (1998) Glycobiology 8:799-811. In the alternative, antibodies can also be raised to various moieties, including fucose, and used in the invention. Methods for raising and purifying antibodies are well known in the art. In addition, monoclonal antibodies can be prepared by any number of techniques that are known in the art, including the technique originally developed by Kohler and Milstein (1975) Nature 256:495-497.

Other proteins that possess carbohydrate recognition domains can also be used as the reagent that is used to detect the biomarker. Proteins having carbohydrate recognition domains have been described, see, e.g., Bouyain S et al. (2002) J. Biol. Chem. 277:22566-72 (Drosophila melanogaster protein CG2958 that recognizes fucose).

In particularly preferred embodiments, lectins are used as the reagent that is used to detect the biomarker. The lectins can be obtained from any organism, including plants, animals, yeast, bacteria, protozoans, and the like. Purified lectins are commercially available, see, e.g., Sigma-Aldrich catalog (St. Louis, Mo.). Lectins can also be isolated from their naturally occurring source, or recombinantly expressed and purified, by means that are well-known to those of skill in the art. The lectin can, but need not be specific for a particular carbohydrate moiety. Fucose-specific lectins have been described. See, e.g., Mansour M H et al. (2005) Immunobiology. 210:335-48; Amano K et al. (2003) Biosci. Biotechnol. Biochem. 67:2277-9; Loris R et al. (2003) J. Mol. Biol. 331:861-70; and, Ishida H et al. (2002) Biosci. Biotechnol. Biochem. 66:1002-8. U.S. Pub. No. 2015/0198610, filed Feb. 3, 2012, which is incorporated herein by reference, discloses various recombinant Aleuria aurantia lectins that are characterized by enhanced binding to core fucosyl moieties. It is contemplated that future-identified or developed lectins are suitable for use as the reagent for detecting the one or more biomarkers in accordance with the present disclosure.

Proteins with lectin-like domains are also suitable for use as the reagent for detecting the one or more biomarkers. Proteins with lectin-like domains are known in the art. See, e.g., Drickamer K (1999) Curr. Opin. Struct. Biol. 9:585-90.

Nucleic acid-based alternatives to lectins can also be used. Such reagents, termed aptamers, take advantage of the huge conformational flexibility of single stranded nucleic acids. From large pools of randomized short nucleic acids, individual molecules with high affinities for numerous non-nucleic acid ligands have been isolated by iterative selection. Advantages of the glycan-binding "lectamer" reagents are that leached DNAs are unlikely to confuse or interfere with downstream analyses. Lectamers can function under uniform binding conditions (pH, ionic strength). Synthetic nucleic acids can be prepared in various derivatized forms (e.g., terminally biotinylated). Target glycans are not limited by existing lectin specificities, substantially expanding existing fractionation and analytical capabilities.

The reagent for detecting a biomarker can be directly labeled with a detectable moiety. In the alternative, a secondary reagent that specifically recognizes the primary reagent, which is labeled with a detectable moiety is used. The secondary reagent can be any molecule, and such as an antibody. The secondary reagent is labeled with a detectable moiety. Detectable moieties contemplated for use in the invention include, but are not limited to, radioisotopes, fluorescent dyes such as fluorescein, phycoerythrin, Cy-3, Cy5, allophycocyanin, DAPI, Texas red, rhodamine, Oregon green, lucifer yellow, and the like, green fluorescent protein, red fluorescent protein, Cyan Fluorescent Protein, Yellow Fluorescent Protein, Cerianthus Orange Fluorescent Protein, alkaline phosphatase, β-lactamase, chloramphenicol acetyltransferase, adenosine deaminase, aminoglycoside phosphotransferase (neor, G418r) dihydrofolate reductase, hygromycin-B-phosphotransferase, thymidine kinase, lacZ (encoding α-galactosidase), and xanthine guanine phosphoribosyltransferase, Beta-Glucuronidase, Placental Alkaline Phosphatase, Secreted Embryonic Alkaline Phosphatase, or Firefly or Bacterial Luciferase. Enzyme tags are used with their cognate substrate. As with other standard procedures associated with the practice of the invention, skilled artisans will be aware of additional labels that can be used. In some embodiments, the reagent or secondary reagent are coupled to biotin, and contacted with avidin or strepatvidin having a detectable moiety tag.

In some embodiments, a moiety that is attached to a polypeptide biomarker by posttranslational modification can be directly labeled and detected, thereby obviating the need for a labeled reagent that specifically recognizes a particular moiety as well as any need for a labeled secondary reagent. For purposes of the present disclosure, detection of the biomarker embraces detection of a moiety that is attached to the biomarker by posttranslational modification. In some embodiments, the moiety attached to the biomarker by posttranslational modification can be separated from the biomarker and directly labeled and detected. For example, and not by way of limitation, carbohydrates and carbohydrate moieties can be directly labeled using various methods that are known in the art. Carbohydrate and carbohydrate moiety labeling kits are commercially available. Carbohydrate and carbohydrate moieties can also be biotinlyated and labeled with avidin- or streptavidin-conjugated detectable moieties, such as those described herein. Non-limiting examples of reagents that can directly label oligosaccharides include 2-aminobenzamide and 2-aminobenzoic acid.

Post-translationally attached moieties can be separated from a polypeptide biomarker by any means suitable in the art, including chemically, for example by treatment with hydrazine or acids such as hydrofluoric acid or trifluoromethanesulfonic acid, enzymatically, for example by treatment with N-glycosidase such as PNGase F, O-glycosidase, endoglycosidases, or exoglycosidases, or by physical means. There are commercially available kits for removing post-translational modifications, including deglycosylation. Chemical bases such as hydrazine, or chemical reagents that lead to beta-elination reactions can also be used in deglysosylation reactions. Other techniques and reagents will be appreciated by those of skill in the art, and are contemplated to be within the scope of the present disclosure.

In some embodiments, the separated, formerly post-translationally attached moieties are purified prior to labeling or detection. Solid or liquid phase extraction techniques, which are known in the art, can be used to purify the separated moieties for further analysis As noted above, total protein biomarkers, such as total alpha-fetoprotein, may be detected using conventional techniques, such as immunoassays, and the reagents that are required for practicing such techniques may be included in the present kits. This is likewise for the kinetic assays based on the respective enzymatic activities of AST and ALT using colorimetric, spectrophotometric, chemiluminescence, chromatography, fluorescence or UV absorbance, radiochemical, and electrochemical techniques for detection.

The present kits include instructions for determining the absence or presence of hepatocellular carcinoma in the subject using an optimized output of a function of the determined age and gender, and the measured amounts of the biomarkers in the biological fluid. The function may be provided in accordance with the description provided above with respect to the instant methods for detecting hepatocellular carcinoma in a subject. The present disclosure also provides specific examples of how one may produce an appropriate function of the determined age and gender, and the measured amounts of the biomarkers.

Also provided herein are methods for assigning a subject to a group having a higher or lower probability of hepatocellular carcinoma comprising removing IgG and IgM proteins from a biological fluid from the subject; measuring the amount of one or more biomarkers in the biological fluid; determining the age and gender of the subject; and, assigning the subject to a group having a higher or lower probability of hepatocellular carcinoma based on an optimized output of a function of the determined age and gender, and the measured biomarkers in the biological fluid.

As provided above in accordance with the presently disclosed methods for detecting hepatocellular carcinoma in a subject, the optimized function of the age, gender, and biomarker amounts yield a value expressing the probability that the subject has hepatocellular carcinoma. The value may reveal that the subject has hepatocellular carcinoma at a level of certainty of about 90% or higher, about 91% or higher, about 92% or higher, about 93% or higher, about 94% or higher, about 95% or higher, about 96% or higher, about 97% or higher, or about 98% or higher. Pursuant to the present methods for assigning a subject to a group having a higher or lower probability of hepatocellular carcinoma, a clinically appropriate decision may be made as to whether the value that the optimized function yields should warrant assigning the subject to a group having a higher or lower probability of hepatocellular carcinoma. For example, a subject may be assigned to a "higher probability" group when the value that is yielded by the optimized function of the age, gender, and biomarker amounts indicates that the subject has hepatocellular carcinoma, and the level of certainty associated with the function is clinically significant. For example, the level of certainty may be at least 50% higher, at least 60% higher, at least 65% higher, at least 70% higher, at least 75% higher, at least 80% or higher, at least 82% or higher, at least 84% or higher, at least 85% or higher, at least 86% or higher, at least 88% or higher, or at least 90% or higher. Skilled pathologists, teamed with biostatisticians, bioinformaticians, and the like can apply the appropriate statistical methodologies to determine whether a value that is yielded by a particular optimized function of the age, gender, and biomarker amounts warrants assignment of the subject to a group having a higher or lower probability of hepatocellular carcinoma.

The present disclosure also provides methods for managing treatment of a subject suspected of having hepatocellular carcinoma comprising removing IgG and IgM proteins from a biological fluid from the subject; measuring the amount of one or more biomarkers in the biological fluid; determining the age and gender of the subject; and, treating the subject based on an optimized output of a function of the determined age and gender, and the measured biomarkers in the biological fluid, wherein the subject is treated for hepatocellular carcinoma when the subject is determined to have that disease based on the output of the function.

Following application of the appropriate statistical assessment, when the output of the optimized function of the determined age and gender and the measured biomarkers in the biological fluid of the subject is indicative of the presence of hepatocellular carcinoma in the subject, the subject may be subjected to treatment in accordance with the present methods. When the subject is asymptomatic, the present methods advantageously permit initiation of a treatment regimen that takes into account the early stage of the hepatocellular carcinoma in the subject. Treatment for early stage hepatocellular carcinoma may be in accordance with accepted medical practice. When, pursuant to the present methods, the subject is determined not to have hepatocellular carcinoma, the subject may be treated for any alternative or precursor condition that may apply. For example, as the subject will have been suspected of having hepatocellular carcinoma, the subject may already have been known to have displayed or subsequently be found to have (e.g., as a result of testing that is motivated by the negative diagnosis of hepatocellular carcinoma) any of the common risk factors, such as alcoholism, Hepatitis B or Hepatitis C, aflatoxin, cirrhosis, nonalcoholic steatohepatitis, hemochromatosis, Wilson's disease, Type 2 diabetes, NASH (nonalcoholic steatohepatitis) or hemophilia. Treatment for any one or more of the conditions representing risk factors for hepatocellular carcinoma may proceed in accordance with appropriate measures as determined by those of ordinary skill in the art. In addition, if a subject is determined not to have hepatocellular carcinoma, the subject can be asked to submit to periodic monitoring that may include testing the subject for hepatocellular carcinoma on one or more future occasions. For purposes of the present methods, "treatment" can encompass subjecting a subject to periodic monitoring in order to confirm whether or not the subject develops hepatocellular carcinoma following an initial determination that the subject does not have hepatocellular carcinoma. For example, pursuant to the present methods, a subject is determined not to have hepatocellular carcinoma based on the output of the optimized function of the determined age and gender and the measured biomarkers in the biological fluid, the subject can be subjected to one or more additional episodes of testing to determine if the subject subsequently develops hepatocellular carcinoma. Additional testing may occur, for example, two months, three months, six months, eight months, one year, 18 months, two years, 30 months, or three years after the initial negative diagnosis of hepatocellular carcinoma, and, for example, every three months, every six months, every year, every 18 months, every two years, every 30 months, every three years, every four years, or every five years, until the subject is found to have hepatocellular carcinoma. The additional testing may be in accordance with the present methods for detecting hepatocellular carcinoma in a subject.

EXAMPLES

The following examples are set forth so as to provide those of ordinary skill in the art with a complete disclosure and description of how the methods, kits, and assays claimed herein may be developed and evaluated, and are intended to be purely exemplary of the invention and are not intended to limit the scope of what the inventors regard as their invention. Efforts have been made to ensure accuracy with respect to numbers (e.g., amounts), but some errors and deviations should be accounted for.

Example 1

Analysis of Clinical Data and Identification of Predictors of HCC

Development of inventive predictors was accomplished using data from two clinical cohorts: one consisted of 115 patients with HCC and 93 patients with cirrhosis (liver function test data available for this cohort), and another of 66 patients with HCC, 38 patients with cirrhosis (liver function test data not available for this cohort).

Twenty-four feature selection algorithms were employed to explore each potential panel constituent (serum biomarkers; patient demographic factors) and combinations. Feature selection algorithms that were applied included: correlation feature selection filter (cfs filter), chi-squared filter, consistency-based filter, linear correlation filter, rank-correlation filter, information gain filter, information ratio filter, system uncertainty, exhaustive search algorithm, greed search forward, greed search backward, Hill climb search, oneR algorithm, random forest filter, relief filter with 3 neighbors, relief filter with five neighbors, step logistic regression, step penalized logistic regression, penalized svm, bestglm (bic), bestglm (aic), robust logistic regression, Bayesian fractional polynomial for GLMs (glmBfp), and Bayesian Model Average (BMA). Subsequently, logistic regression was applied with the subsets of predictors, which were provided by the 24 feature selection algorithms. There were 21 subset features that were selected from the feature selection algorithms and market basket analysis. To this, full predictors and AFP were added to the conference subset, and from this, 23 logistic regression algorithms were built. To judge the fitness of each regression, the inventors derived AIC, $R^2$, Dxy, likelihood ratio test, Pearson's goodness-of-fit, log-likelihood, deviation statistic, tau-a, NRI, and the Area Under the ROC curve (AUROC) of apparent validation. From these criteria and tests, four logistic regression models that had the highest fitness were selected for further evaluation. To avoid over-fitting, leave-one-out cross-validation, bootstrap-validation and three-fold cross-validation were applied in order to validate the four candidate models.

Fourteen biomarker, clinical, and demographic variables were assessed: alanine aminotransferase (ALT), aspartate aminotransferase (AST), bilirubin (BIL), albumin (ALB), platelets (PLT), alkaline phosphatase (ALK), white blood cells (WBC), alpha-fetoprotein (AFP), fucosylated A1AT, fucosylated low molecular weight (LMW) kininogen, fucosylated fetuin A, fucosylated hemopexin, age and gender. AFP values were distributed in a wide range (1 to 347,000 ng/ml) and were log transformed for further analysis. As the data distribution of the remaining factors did not influence the statistical analysis and algorithm exploration, the original data formats were used.

Preliminary analysis indicated that AFP, ALK, AST, age and male gender were positively associated with probability of HCC. There was a high male ratio in the HCC group, with an odds ratio of 1.75, $\chi^2=5.36$, df=1, p=0.02056. It was found that inclusion of AFP yielded superlatively high AUROC values for the discrimination of HCC. When AFP was used in the absence of fucosylated biomarkers, AUROC values varied from 0.8016 for AFP alone to 0.9066 with inclusion of four additional factors (age, gender, ALK, ALT). Increasing the number of variables did not change the AUROC beyond this value, suggesting the need for the inclusion of new biomarkers to drive detection.

To this end, an evaluation of panels containing various biomarkers was carried out. The combination of AFP, fucosylated low molecular weight (LMW) kininogen, fucosylated A1AT, age, and gender yielded an AUROC of 0.9405. Addition of AST and ALK increased the AUROC to 0.9835. Elimination of fucosylated A1AT reduced the AUROC modestly to 0.9826. This latter minimal panel consisting of fucosylated LMW kininogen, AFP, AST, ALK, age and gender led to Algorithm A, below, and was employed in the generation of the patient subset data (by early stage and AFP-negative disease) shown in FIGS. 1A-1C.

Algorithm A $$P = \frac{1}{1 + \exp(-[-17.7221 + (0.1646*\text{age}) + (3.9453*\text{male}) + (2.4343*\log AFP) + (1.3748*\text{Kininogen}) + (0.0239*ALK) + (-0.0222*AST)])}$$

Figure 1B:
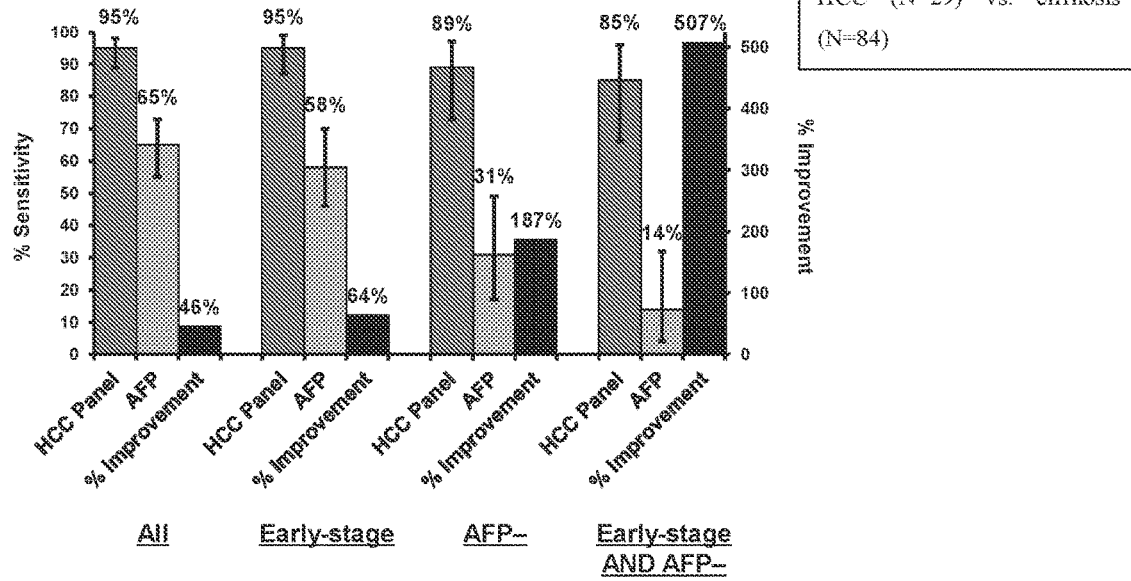
Figure 1C:
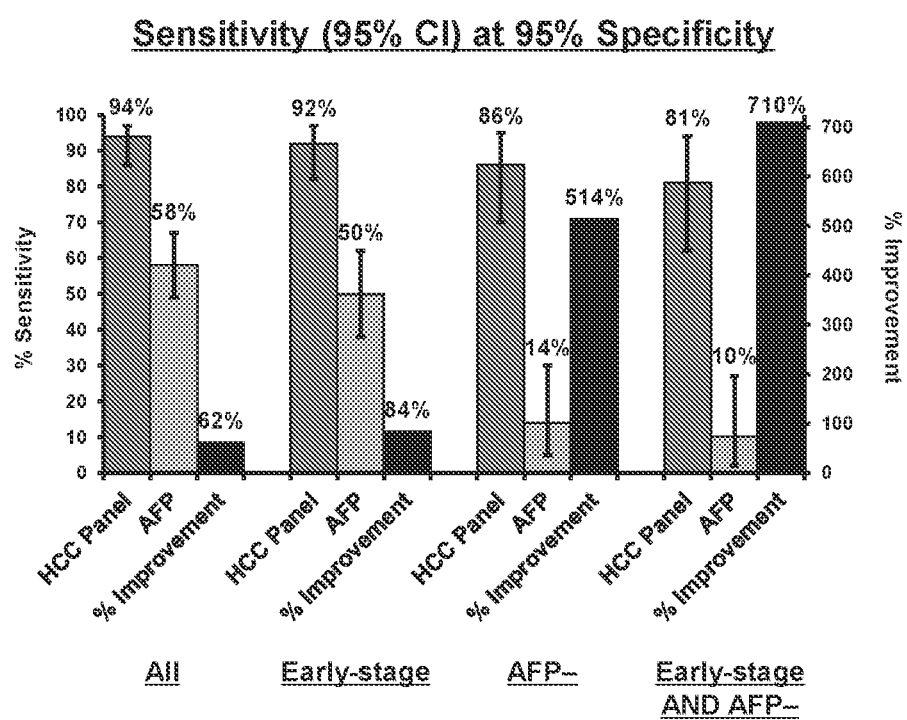

FIGS. 1A-1C depict the results of an evaluation of a panel consisting of fucosylated low molecular weight kininogen, alpha-fetoprotein, aspartate aminotransferase (AST), alkaline phosphatase (ALK), age, and gender. The panel was evaluated within one of three different cohorts of HCC and cirrhosis patients. The three patient cohorts respectively had the characteristics described in Table 1, below:

TABLE 1

| Patient Set | Total | HCC | Cirrhosis | Early HCC | Late HCC | HCC AFP <20 ng/mL | Cirrhosis AFP <20 ng/mL | Early HCC <20 ng/mL | Late HCC <20 ng/mL |
|---|---|---|---|---|---|---|---|---|---|
| a | 208 | 115 | 93 | 69 | 46 | 39 | 84 | 29 | 10 |
| b | 104 | 66 | 38 | 48 | 17 | 17 | 34 | 14 | 3 |
| c | 40 | 20 | 20 | 6 | 14 | 7 | 18 | 2 | 5 |

In the population used to generate the data in FIG. 1, the HCC etiology was 61% HCV, 6% HBV, and 33% other, and the cirrhosis etiology was 48% HCV, 10% HBV, and 42% other. FIG. 1A summarizes data for the areas under the receiver operating characteristic curves (AUROCs) for the discrimination of all patients with HCC (N=115) from all patients with cirrhosis (N=93); with early-stage HCC (N=69) from cirrhosis (N=93); with AFP negative HCC (N=39) from AFP negative cirrhosis (N=84); and with both early-stage and AFP negative HCC (N=29) from AFP negative cirrhosis (N=84). 95% confidence intervals (CIs) were non-overlapping in all cases. FIG. 1B summarizes the sensitivity values at 90% specificity cutoffs for discrimination of the same respective patient groups in the same study, and FIG. 1C summarizes the sensitivity values at 95% specificity cutoffs for discrimination of the same respective patient groups in the same study.

Algorithm B $$P = \frac{1}{1 + \exp(-[-11.056 + (0.106 * \mathrm{Age}) + (-1.419 * \mathrm{Male}) + (2.211 * \log AFP) + (4.329 * \mathrm{Fetuin A}) + (-2.091 * \mathrm{Hemopexin})])}$$

A further algorithm was used to conduct a separate test of the same panel members (panel 4, shown in Table 2, below), and yielded an AUC of 0.8461. When hemopexin was replaced by kininogen (panel 5b in Table 2), the AUC increased to 0.8661.

A summary of the results of the assessment of panels that included age, alpha fetoprotein, and other specified biomarkers is provided below in Table 2.

TABLE 2

| Panel No. | Fucosylated Biomarkers | | | | Non-Fucosylated Biomarkers | | | | | Demographic Values | | AUC | Patient Set |
|---|---|---|---|---|---|---|---|---|---|---|---|---|---|
| | Kininogen | A1AT | Fetuin A | Hemopexin | Total AFP | AST | ALT | ALK | Albumin | Age | Gender | | |
| 1 | ✓ | | | | ✓ | ✓ | | ✓ | | ✓ | ✓ | 0.9826 | a |
| 2 | ✓ | ✓ | | | ✓ | ✓ | | ✓ | | ✓ | ✓ | 0.9835 | a |
| 3 | | | ✓ | | ✓ | | | | | ✓ | ✓ | 0.9378 | b |
| 4 | | | | ✓ | ✓ | | | | | ✓ | ✓ | 0.8461 | b |
| 5a | ✓ | | | | ✓ | | | | | ✓ | ✓ | 0.9378 | a |
| 5b | ✓ | | | | ✓ | | | | | ✓ | ✓ | 0.8661 | b |
| 6 | | | ✓ | ✓ | ✓ | | | | | ✓ | ✓ | 0.9653 | b |
| 7 | ✓ | | ✓ | | ✓ | | | | | ✓ | ✓ | 0.9378 | b |
| 8a | ✓ | ✓ | | | ✓ | | | | | ✓ | ✓ | 0.9405 | a |
| 8b | ✓ | ✓ | | | ✓ | | | | | ✓ | ✓ | 0.8732 | b |
| 9 | ✓ | ✓ | ✓ | | ✓ | | | | | ✓ | ✓ | 0.9391 | a |
| 10 | ✓ | | ✓ | | ✓ | | | | | ✓ | ✓ | 0.9440 | b |
| 11 | ✓ | | | | ✓ | | ✓ | ✓ | | ✓ | ✓ | 0.9744 | a |
| 12 | ✓ | | | | ✓ | | | ✓ | | ✓ | ✓ | 0.9759 | a |
| 13 | ✓ | | | | ✓ | ✓ | | | | ✓ | ✓ | 0.9461 | a |
| 14 | ✓ | | | | ✓ | | ✓ | | | ✓ | ✓ | 0.9371 | a |
| 15 | | ✓ | | | ✓ | | | | ✓ | | ✓ | 0.9650 | c |

As noted above, the incorporation of AST and ALK into the developed model increased the AUC from 0.9405 to 0.9835. The incorporation of these two clinical variables unexpectedly offset the need for inclusion of one of the fucosylated biomarkers, in this case, fucosylated A1AT: when AST and ALK were added to the equation and fucosylated A1AT was dropped from the algorithm, the AUC remained at 0.9826, suggesting that a highly predictive basic model incorporated age, gender, kininogen, ALK, and AST.

Previous work identified fucosylated Fetuin-A and fucosylated hemopexin as very good individual indicators of hepatocellular carcinoma (Comunale, M A, et al. J. Proteome Res. 2009; 8; 595-602). An assessment was conducted as to the contribution of these individual fucosylated biomarkers to a panel that also included age, gender, and AFP (log). Algorithm B, shown below, was employed in order to test a panel including fucosylated Fetuin-A and fucosylated hemopexin:

Tables 3A and 3B, below, provides AUROCs (95% confidence intervals), sensitivities (95% confidence intervals) at indicated fixed specificities and positive (LR+) and negative (LR−) likelihood ratios for the discrimination by Panel No. 1 (as shown above in Table 2) of the following patients: (1) HCC (N=115) from cirrhosis (N=93); (2) early-stage HCC (UNOS T1/2; N=69) from cirrhosis (N=93); (3) AFP-negative HCC (<20 ng/mL; N=39) from AFP-negative cirrhosis (<20 ng/mL; N=84); and (4) early-stage (UNOS T1/2) and AFP-negative HCC (<20 ng/mL; N=29) from AFP-negative cirrhosis (<20 ng/mL; N=84). [HCC etiology (%)=HCV (61); HBV (6); other (33); HCC gender (M/F %)=73/27; Cirrhosis etiology (%)=HCV (48); HBV (10); other (42); Cirrhosis gender (M/F %)=51/49]. These data were obtained using HCC panel scores (P values) obtained directly from Algorithm A.

TABLE 3A

| | All HCC (N = 115) vs All Cirrhosis (N = 93) | | Early HCC (UNOS T1/2; N = 69) vs All Cirrhosis (N = 93) | |
|---|---|---|---|---|
| | HCC Panel | AFP | HCC Panel | AFP |
| AUROC (95% CI) | 0.98 (0.97-1.00) | 0.83 (0.78-0.89) | 0.98 (0.96-1.00) | 0.79 (0.72-0.86) |
| Sensitivity (95% CI) at Fixed Specificity: | | | | |
| 95%: | 94% (86-97%) | 58% (49-67%) | 92% (82-97%) | 50% (38-62%) |
| 90%: | 95% (89-98%) | 65% (55-73%) | 95% (87-99%) | 58% (46-70%) |
| 85%: | 96% (90-99%) | 70% (61-78%) | 97% (89-99%) | 63% (50-74%) |
| LR+ at Fixed Specificity: | | | | |
| 95%: | 19 | 12 | 18 | 10 |
| 90%: | 9.5 | 6.5 | 9.5 | 5.8 |
| 85%: | 6.4 | 4.7 | 6.5 | 4.2 |
| LR− at Fixed Specificity: | | | | |
| 95%: | 0.063 | 0.44 | 0.084 | 0.53 |
| 90%: | 0.056 | 0.39 | 0.056 | 0.47 |
| 85%: | 0.047 | 0.35 | 0.035 | 0.44 |

TABLE 3B

| | AFP-negative HCC (<20 ng/mL; N = 39) vs AFP-negative Cirrhosis (<20 ng/mL; N = 84) | | Early/AFP-negative HCC (N = 29) vs AFP-negative Cirrhosis (N = 84) | |
|---|---|---|---|---|
| | HCC Panel | AFP | HCC Panel | AFP |
| AUROC (95% CI) | 0.97 (0.95-1.00) | 0.64 (0.53-0.75) | 0.96 (0.92-0.99) | 0.59 (0.47-0.71) |
| Sensitivity (95% CI) at Fixed Specificity: | | | | |
| 95%: | 86% (70-95%)[1] | 14% (5-30%)[1] | 81% (62-94%) | 10% (2-27%) |
| 90%: | 89% (73-97%) | 31% (17-49%) | 85% (66-96%) | 14% (4-32%) |
| 85%: | 91% (77-98%) | 31% (17-49%)[2] | 89% (71-98%) | 24% (10-44%) |
| LR+ at Fixed Specificity: | | | | |
| 95%: | 22[1] | 3.5[1] | 16 | 2.0 |
| 90%: | 8.9 | 3.1 | 8.5 | 1.4 |
| 85%: | 6.1 | 2.2[2] | 5.9 | 1.6 |
| LR− at Fixed Specificity: | | | | |
| 95%: | 0.15[1] | 0.90[1] | 0.20 | 0.95 |
| 90%: | 0.12 | 0.77 | 0.17 | 0.96 |
| 85%: | 0.11 | 0.80[2] | 0.13 | 0.89 |

[1] At 96% specificity.
[2] At 86% specificity.

Tables 4A and 4B, below, provide AUROCs (95% confidence intervals) and sensitivities (95% confidence intervals) at indicated fixed specificities for the discrimination by Panel No. 11 (as shown above in Table 2) of the following patients: (1) HCC (N=115) from cirrhosis (N=93); (2) early-stage HCC (UNOS T1/2; N=69) from cirrhosis (N=93); (3) AFP-negative HCC (<20 ng/mL; N=39) from AFP-negative cirrhosis (<20 ng/mL; N=84); and (4) early-stage (UNOS T1/2) and AFP-negative HCC (<20 ng/mL; N=29) from AFP-negative cirrhosis (<20 ng/mL; N=84). [HCC etiology (%)=HCV (61); HBV (6); other (33); HCC gender (M/F %)=73/27; Cirrhosis etiology (%)=HCV (48); HBV (10); other (42); Cirrhosis gender (M/F %)=51/49]. These data were obtained using Algorithm A (except that AST values were replaced by ALT values) and three-fold cross validation.

TABLE 4A

|  | All HCC (N = 115) vs All Cirrhosis (N = 93) | | Early HCC (UNOS T½; N = 69) vs All Cirrhosis (N = 93) | |
| --- | --- | --- | --- | --- |
|  | HCC Panel | AFP | HCC Panel | AFP |
| AUROC (95% CI) | 0.977 (0.960-0.994) | 0.844 (0.787-0.902) | 0.971 (0.947-0.994) | 0.803 (0.723-0.878) |
| Sensitivity (95% CI) at Fixed Specificity: | | | | |
| 95% | 90% (80-97%) | 60% (48-71%) | 86% (68-97%) | 53% (38-67%) |
| 90% | 94% (86-99%) | 66% (53-77%) | 92% (81-98%) | 59% (44-73%) |
| 85% | 96% (90-99%) | 69% (57-80%) | 95% (86-100%) | 62% (48-76%) |

TABLE 4B

|  | AFP-negative HCC (<20 ng/mL; N = 39) vs AFP-negative Cirrhosis (<20 ng/mL; N = 84) | | Early/AFP-negative HCC (N = 29) vs AFP-negative Cirrhosis (N = 84) | |
| --- | --- | --- | --- | --- |
|  | HCC Panel | AFP | HCC Panel | AFP |
| AUROC (95% CI) | 0.965 (0.935-0.996) | 0.637 (0.523-0.751) | 0.970 (0.936-1) | 0.597 (0.473-0.721) |
| Sensitivity (95% CI) at Fixed Specificity: | | | | |
| 95% | 82% (62-97%) | 9% (0-35%) | 89% (70-100%) | 0% (0-24%) |
| 90% | 88% (74-97%) | 24% (3-44%) | 89% (77-100%) | 14% (0-35%) |
| 85% | 91% (77-100%) | 33% (12-53%) | 92% (77-100%) | 19% (4-46%) |

Upon review of the data as a whole, it was unexpectedly the case that the variables that contributed to the highest performing panels tended to be those that were the least effective as indicators of hepatocellular carcinoma on an individual basis. For example, hemopexin yielded the highest AUC value when used alone (0.8695 in patient set b), and A1AT (patient set a), AFP (patient set a), and kininogen (patient set a) yielded the lowest AUC values when used alone (0.7395, 0.8346 and 0.8192, respectively), but the latter contributed to higher performing panels than those containing hemopexin. It was learned from these data that it is not possible to predict the contribution of a particular biomarker to a panel based on the individual ability of that biomarker to determine the presence of hepatocellular carcinoma.

The data also reveal the ability of the tested panels to permit detection of early stage hepatocellular cellular carcinoma, AFP negative hepatocellular cellular carcinoma, and early stage hepatocellular cellular carcinoma that is also AFP negative hepatocellular cellular carcinoma.

Example 2

Identification of IgG and IgM as Assay Contaminants

Plate-based assays for the detection of hepatocellular carcinoma have conventionally been hampered by the presence of heterophilic antibodies, and potentially other lectin binding contaminates. Such contaminants are known to lead to false positive results. A study was undertaken in order to identify contaminating lectin-reactive factors present in the serum of those with cirrhosis and liver cancer. As described infra, the present inventors identified IgM as the contaminating lectin reactive factor, and when IgM was removed from the serum prior to lectin-ELISA, specific protein-associated, lectin reactive signals could be detected. This method was used in two independent sample sets to validate the method and also to validate the performance of the fucosylated glycoforms as biomarkers of hepatocellular carcinoma.

Methods

Serum samples were obtained from the blood of each test subject, as was demographic and clinical information for the patient population. Consecutive patients with HCC, and patients with cirrhosis that were age-, gender-, and race/ethnicity-matched to the HCC patients, were enrolled in the study. The diagnosis of HCC was made by histopathology, including all T1 lesions, and, if histopathology was not available by two imaging modalities (ultrasound, magnetic resonance imaging, or computed tomography) showing a vascular enhancing mass>2 cm. Diagnosis of cirrhosis was based on liver histology or clinical, laboratory and imaging evidence of hepatic decompensation or portal hypertension. Each of the patients with cirrhosis had a normal ultrasound and, if serum AFP was elevated, no liver mass was shown by a MRI of the liver within three months prior to enrollment, and another MRI six months after enrollment. The cirrhotic controls were followed for a median of 12 months (range: 7-18 months) after enrollment, and no one had developed HCC. Tumor staging was determined using the United Network of Organ Sharing-modified TNM staging system for HCC. Early HCC was defined as T1 (single lesion <2 cm in diameter) and T2 (single lesion between 2 and 5 cm in diameter; or <3 lesions each <3 cm in diameter) lesions, which met criteria for liver transplantation in the United States. A 20-ml blood sample was drawn from each subject, spun, aliquoted, and the resulting serum was stored at −80° C. until testing. Blood samples were drawn prior to initiation of HCC treatment. AFP was tested using commercially available immunoassays utilizing enhanced chemiluminescence.

Lectin FLISA

Briefly, to remove the fucosylation of the capture antibody (Mouse anti-human AAT or rabbit anti-fetuin, AbD Serotec, Raleigh, N.C.) the antibody was incubated with 10 mM sodium periodate for 1 hour at 4° C. An equal volume of ethylene glycol was added and the oxidized antibody brought to a concentration of 10 μg/mL with sodium carbonate buffer, pH 9.5. Antibody (5 μg/well) was added to the plate and, following incubation, was washed with 0.1% Tween® 20 (polysorbate 20)/PBS 7.4 and blocked overnight with 3% BSA/PBS. For analysis, 5 μl of serum was diluted in 95 μl of Heterophilic Blocking Tubes™ (Scantibodies Laboratory, Inc., Santee, Calif.) and was incubated at room temperature for 1 hour. Subsequently, samples were added to the plates for 2 hours and washed five times in lectin incubation buffer (10 mM Tris pH 8.0, 0.15 M NaCl, 0.1% Tween 20®) before fucosylated protein was detected with a biotin conjugated Aleuria aurantia (AAL) lectin (Vector Laboratories, Burlingame, Calif.). Bound lectin was detected using IRDye™ 800 Conjugated streptavidin and signal intensity measured using the Odyssey® Infrared Imaging System (LI-COR Biotechnology, Lincoln, Nebr.). In all cases, signal intensity was compared to signals detected with commercially purchased human serum (Sigma-Aldrich, St. Louis, Mo.). It is noted that the lectin-FLISA detects the amount of fucosylation present on an equal amount of captured molecules from each patient sample and is performed in a manner that is independent of the total amount of protein in any given patient.

Proteomic Identification of Contaminating Factors

Lectin-Western

Serum was depleted of IgG using protein AIG coated agarose beads and A1AT immunoprecipitated using magnetic Dynabeads® (Thermo Fisher Scientific Inc., Waltham, Mass.) coated with monoclonal anti-A1AT (AbD Serotec, Raleigh, N.C.). Subsequently, A1AT was eluted and resolved via SDS-PAGE. The fucosylated A1AT was detected using biotin conjugated Aleuria aurantia lectin (AAL). Bound AAL was visualized using IRDye™ 800 Conjugated streptavidin and signal intensity measured using the Odyssey® Infrared Imaging System (LI-COR Biotechnology, Lincoln, Nebr.). Subsequently, A1AT was detected using a poly-clonal anti-A1AT (Sigma-Aldrich, St. Louis, Mo.) and bound antibody detected using an IRDye™ 700 Conjugated anti-rabbit antibody.

In previous analysis of a small sample set of 40 patients, 20 with liver cirrhosis and 20 with liver cirrhosis and HCC, the method of a lectin-ELISA was unable to specifically detect altered fucosylation of a given protein. For example, a lectin ELISA would be performed for fucosylated alpha-1-anti-trypsin (A1AT). In this method, antibody to A1AT, which has been modified to remove its inherent fucosylation, is coated to the bottom of a 96 well plate. Serum that is depleted of IgG using protein A/G is added, and the fucosylation level of captured A1AT is detected using a recombinant Aleuria aurantia lectin (AAL). When such an assay is done using HCC serum, a lectin reactive signal is observed. However, it was not possible to compete out this signal using non fucosylated A1AT, even when non-fucosylated A1AT had bound to the capture antibody. In addition, the use of a non-specific antibody, such as AFP in an AFP-negative patient, led to the same non-specific signal. Tryptic digestion of the sample prior to analysis confirmed that the signal was protein-based.

Identification of IgM as a Potential Contaminant

In an effort to identify the non-specific lectin reactive material found in serum, a lectin ELISA was performed in 96 well plates for A1AT. Plates were incubated with serum using conditions identical to a normal lectin ELISA, but before lectin was added, sample was incubated with SDS lysis buffer and the sample examined via SDS-PAGE and lectin blotting with fucose binding lectin by colloidal coomassie brilliant blue staining, or by blotting for the presence of human A1AT. Strong lectin staining was observed with a band of ~80 kD with a weaker band observed at 50 kD. While the 50 kD band was also observed following staining with colloidal coomassie brilliant blue and by staining with the A1AT antibody, the ~80 kD band was not observed via staining with either colloidal coomassie brilliant blue or A1AT lectin blotting. This suggested that the non-specific lectin reactive material in these samples was a 80 kD glycoprotein that was highly fucosylated. Subsequently, wells treated identically were collected following ELISA capture and examined proteomically following digestion with trypsin. The list of glycoproteins identified in these samples are shown in Table 5, below, and the two major proteins were observed that were similar in size to that observed in the lectin blotting: complement B and the IgM heavy chain.

TABLE 5

| Associated Gene | Protein Name | Spectral Counts |
| --- | --- | --- |
| KRT1 | keratin 1 [Source: HGNC Symbol; Acc: HGNC:6412] | 450 |
| APOA1 | apolipoprotein A-I [Source: HGNC Symbol; Acc: HGNC:600] | 345 |
| KRT9 | keratin 9 [Source: HGNC Symbol; Acc: HGNC:6447] | 283 |
| KRT10 | keratin 10 [Source: HGNC Symbol; Acc: HGNC:6413] | 224 |
| APOE | apolipoprotein E [Source: HGNC Symbol; Acc: HGNC:613] | 214 |
| KRT2 | keratin 2 [Source: HGNC Symbol; Acc: HGNC:6439] | 161 |
| SERPINA1 | Serpin peptidase inhibitor, clade A (Alpha-1 antiproteinase, antitrypsin), member 1, isoform CRA_a [Source: UniProtKB/TrEMBL; Acc: A0A024R6I7] | 131 |
| | serpin peptidase inhibitor, clade A (alpha-1 antiproteinase, antitrypsin), member 1 [Source: HGNC Symbol; Acc: HGNC:8941] | 5 |

TABLE 5-continued

| Associated Gene | Protein Name | Spectral Counts |
|---|---|---|
| KRT16 | keratin 16 [Source: HGNC Symbol; Acc: HGNC:6423] | 126 |
| KRT14 | keratin 14 [Source: HGNC Symbol; Acc: HGNC:6416] | 85 |
| KRT5 | keratin 5 [Source: HGNC Symbol; Acc: HGNC:6442] | 76 |
| C1QC | complement component 1, q subcomponent, C chain [Source: HGNC Symbol; Acc: HGNC:1245] | 65 |
| C1QB | complement component 1, q subcomponent, B chain [Source: HGNC Symbol; Acc: HGNC:12421 | 62 |
| C1S | complement component 1, s subcomponent [Source: HGNC Symbol; Acc: HGNC:1247] | 52 |
| APOB | apolipoprotein B [Source: HGNC Symbol; Acc: HGNC:603] | 49 |
| A2M | alpha-2-macroglobulin [Source: HGNC Symbol; Acc: HGNC:7] | 49 |
| F2 | coagulation factor II (thrombin) [Source: HGNC Symbol; Acc: HGNC:3535] | 49 |
| APOC1 | apolipoprotein C-I [Source: HGNC Symbol; Acc: HGNC:607] | 46 |
| KRT6A | keratin 6A [Source: HGNC Symbol; Acc: HGNC:6443] | 44 |
| HBB | hemoglobin, beta [Source: HGNC Symbol; Acc: HGNC:4827] | 43 |
| CLU | clusterin [Source: HGNC Symbol; Acc: HGNC:2095] | 40 |
| DSP | desmoplakin [Source: HGNC Symbol; Acc: HGNC:3052] | 39 |
| VTN | vitronectin [Source: HGNC Symbol; Acc: HGNC:12724] | 36 |
| SAA2-SAA4 | SAA2-SAA4 readthrough [Source: HGNC Symbol; Acc: HGNC:39550] | 31 |
| APOA4 | apolipoprotein A-IV [Source: HGNC Symbol; Acc: HGNC:602] | 28 |
| IGHG1 | immunoglobulin heavy constant gamma 1 (G1m marker) [Source: HGNC Symbol; Acc: HGNC:5525] | 26 |
| APOA2 | apolipoprotein A-II [Source: HGNC Symbol; Acc: HGNC:601] | 26 |
| C3 | complement component 3 [Source: HGNC Symbol; Acc: HGNC:1318] | 22 |
| HBA2 | hemoglobin, alpha 2 [Source: HGNC Symbol; Acc: HGNC:4824] | 21 |
| DSG1 | desmoglein 1 [Source: HGNC Symbol; Acc: HGNC:3048] | 19 |
| KRT17 | keratin 17 [Source: HGNC Symbol; Acc: HGNC:6427] | 19 |
| IGHM | immunoglobulin heavy constant mu [Source: HGNC Symbol; Acc: HGNC:5541] | 19 |
| HRNR | homerin [Source: HGNC Symbol; Acc: HGNC:20846] | 17 |
| C1R | complement component 1, r subcomponent [Source: HGNC Symbol; Acc: HGNC:1246] | 17 |
| CD14 | CD14 molecule [Source: HGNC Symbol; Acc: HGNC:1628] | 15 |
| APOC3 | apolipoprotein C-III [Source: HGNC Symbol; Acc: HGNC:610] | 15 |
| AGT | angiotensinogen (serpin peptidase inhibitor, clade A, member 8) [Source: HGNC Symbol; Acc: HGNC:333] | 14 |
| TRAJ56 | T cell receptor alpha joining 56 [Source: HGNC Symbol; Acc: HGNC:12088] | 14 |
| IGHA1 | immunoglobulin heavy constant alpha 1 [Source: HGNC Symbol; Acc: HGNC:5478] | 12 |
| ALB | albumin [Source: HGNC Symbol; Acc: HGNC:399] | 12 |

Subsequently, the same lectin ELISA experiment described above was repeated with anti-complement B and anti-IgM antibodies. While there was no staining in the captured material with the anti-complement B antibody, immunblotting showed that the 80 kD lectin reactive material found in these samples was IgM heavy chain. The 80 kD band represents IgM heavy chain that is indicative of the entire IgM molecule. In total, there are 10 heavy chains per one IgM molecule.

In an effort to remove native IgM from the serum samples, methods were developed to remove this material from serum before lectin-ELISA analysis. Initially, protein L was used, but yielded unsatisfactory results. A method was subsequently used that involved incubating serum with 20 µl of Pierce™ Protein A/G Plus (Thermo Fisher Scientific Inc., Waltham, Mass.) for one hour, followed by filtration of the mix in a 100 kD spin filter in order to remove both IgG and IgM from the serum prior to lectin ELISA. When this method was used, IgG and IgM was efficiently removed from the serum, as determined by both immunoblotting or by lectin blotting. Subsequently, after the removal of IgM and IgG using this method, it was possible to block lectin reactive A1AT signal using non-fucosylated A1AT, demonstrating the finding that the presence of IgG and IgM were responsible to the contaminating signal observed in these samples.

The ability of this method to be used for the analysis of fucosylated glycoforms of A1AT was examined using a small sample set where Lectin-ELISA methods had previously failed. This set consisted of 20 patients with cirrhosis and 20 patients with HCC in the background of cirrhosis. Importantly, in this set, lectin-western data showing lectin-reactive A1AT was determined and acts as the gold standard for the lectin-ELISA (Comunale, Mass., et al. Proteomics Clin. Appl. 2013; 7; 690-700) and permitted a comparison between the performance of the lectin-ELISA with and without filtration. Using the non-filtration method, the mean value of the cirrhotic sample was 3.2 (±2.0) and the HCC sample was 2.9 (±1.8). There is no statistical difference between the lectin reactive signal in these samples (p=0.74). The AUROC of this assay was 0.578. In contrast, using the inventive filtration method, the lectin ELISA result in a mean value of 1.4 (±0.75) in the cirrhotic sample and 2.4 (±1.1) in the HCC samples. This difference was statistically different (P=0.0016). When comparing the samples before filtration and after filtration, there was statistical difference between the cirrhosis samples before and after filtration (p=0.0005) but not between the HCC samples before and after filtration (p=0.5249).

The AUROC of the comparison between the HCC and cirrhosis samples after filtration was 0.788, which was nearly identical to that observed by the lectin-western (Comunale, et al., 2013). Importantly, there was a high degree of correlation between the lectin-western and the lectin-ELISA following filtration. Importantly, every sample that was positive for the lectin-ELISA following filtration was shown to be positive by the lectin-western, and every sample shown to be negative by the lectin-ELISA following filtration was shown to be negative by the lectin-western.

This assay was subsequently used to assess 80 independent samples for the presence of fucosyated alpha-1 antitrypsin and fucosylated kininogen. Samples were examined using the filtration lectin-ELISA and the un-filtered lectin-ELISA. While the un-filtered analysis resulted in no difference between the HCC and control samples, the filtered analysis did yield a statistically significant difference.

Alternative Procedure for Removal of IgG and IgM Contaminants.

An alternative method was developed to remove IgG and IgM whereby serum was incubated with PEG-8000, centrifuged, and the supernatant assayed in the lectin ELISA. For example, for the analysis of fucosylated A1AT or fucosylated fetuin A, 2 µL of serum was added to 8 µL PBS and subsequently 6 µL of aqueous 40% PEG-8000 solution was added for a final PEG-8000 concentration of 15%. The sample was mixed by drawing it into and expelling it from a pipet 10-20 times and then vortexing briefly. The sample was next incubated on a shaking machine at 1000-1500 rpm for 30 minutes, and then incubation was continued with slow shaking at 4° C. overnight. The next morning the sample was centrifuged at 14,000 rpm at 4° C., and the supernatant quickly transferred to a fresh tube prior to lectin ELISA. Efficacy of the IgG and IgM removal was confirmed using similar methodologies as for the original procedure for removing the immunoglobulins, for example, by immunoblotting or by lectin blotting.

What is claimed:

1. A method for detecting hepatocellular carcinoma in a subject comprising:
  measuring the amount of biomarkers comprising
  alpha-fetoprotein, fucosylated kininogen, alkaline phosphatase, and aspartate aminotransferase;
  alpha-fetoprotein, fucosylated kininogen, alkaline phosphatase, aspartate aminotransferase, and fucosylated alpha-1-antitrypsin;
  alpha-fetoprotein, fucosylated kininogen, alkaline phosphatase, aspartate aminotransferase, and fucosylated fetuin-A;
  alpha-fetoprotein, fucosylated kininogen, alkaline phosphatase, aspartate aminotransferase, fucosylated fetuin-A, and fucosylated alpha-1-antitrypsin;
  alpha-fetoprotein and fucosylated fetuin-A;
  alpha-fetoprotein and fucosylated hemopexin;
  alpha-fetoprotein and fucosylated kininogen;
  alpha-fetoprotein, fucosylated fetuin-A, and fucosylated hemopexin;
  alpha-fetoprotein, fucosylated fetuin-A, and fucosylated kininogen;
  alpha-fetoprotein, fucosylated kininogen, and alkaline phosphatase;
  alpha-fetoprotein, fucosylated alpha-1 antitrvpsin, and fucosylated kininogen;
  or,
  alpha-fetoprotein, fucosylated alpha-1 antitrypsin, fucosylated fetuin A, and fucosylated kininogen,
  in a biological fluid from the subject or in a separate sample derived from the biological fluid, but prior to measuring the amount of a biomarker that is a fucose-containing glycoform, removing IgG and IgM proteins from the biological fluid from the subject or the separate sample derived from the biological fluid;
  determining the age and gender of the subject; and,
  determining the absence or presence of hepatocellular carcinoma in the subject using an output of a function of the determined age and gender, and the measured biomarkers in the biological fluid.

2. A method for managing treatment of a subject suspected of having hepatocellular carcinoma comprising:
  measuring the amount of biomarkers comprising
  alpha-fetoprotein, fucosylated kininogen, alkaline phosphatase, and aspartate aminotransferase;
  alpha-fetoprotein, fucosylated kininogen, alkaline phosphatase, aspartate aminotransferase, and fucosylated alpha-1-antitrypsin;
  alpha-fetoprotein, fucosylated kininogen, alkaline phosphatase, aspartate aminotransferase, and fucosylated fetuin-A;
  alpha-fetoprotein, fucosylated kininogen, alkaline phosphatase, aspartate aminotransferase, fucosylated fetuin-A, and fucosylated alpha-1-antitrypsin;
  alpha-fetoprotein and fucosylated fetuin-A;
  alpha-fetoprotein and fucosylated hemopexin;
  alpha-fetoprotein and fucosylated kininogen;
  alpha-fetoprotein, fucosylated fetuin-A, and fucosylated hemopexin;
  alpha-fetoprotein, fucosylated fetuin-A, and fucosylated kininogen;
  alpha-fetoprotein, fucosylated kininogen, and alkaline phosphatase;
  or,
  alpha-fetoprotein, fucosylated alpha-1 antitrypsin, fucosylated fetuin A, and fucosylated kininogen,
  in a biological fluid from the subject or in a separate sample derived from the biological fluid, but prior to measuring the amount of a biomarker that is a fucose-containing glycoform,
  removing IgG and IgM proteins from a biological fluid from the subject or the separate sample derived from the biological fluid;
  determining the age and gender of the subject; and,
  treating the subject based on an optimized output of a function of the determined age and gender, and the measured biomarkers in the biological fluid, wherein the subject is treated for hepatocellular carcinoma when the subject is determined to have that disease based on the output of the function.

3. The method according to claim 1, wherein the function comprises respective weighting coefficients for the determined age and gender, and for the measured amounts of the measured biomarkers.

4. The method according to claim 1, wherein the biomarkers are alpha-fetoprotein, fucosylated kininogen, alkaline phosphatase, and aspartate aminotransferase.

5. The method according to claim 1, wherein the biomarkers are alphafetoprotein, fucosylated kininogen, alkaline phosphatase, aspartate aminotransferase, and fucosylated alpha-1-antitrypsin.

6. The method according to claim 1, wherein the biomarkers are alphafetoprotein, fucosylated kininogen, alkaline phosphatase, aspartate aminotransferase, and fucosylated fetuin-A.

7. The method according to claim 1, wherein the IgG is removed by incubating the biological fluid or separate sample derived from the biological fluid with Protein A/G, and the IgM is removed by passing the biological fluid or separate sample derived from the biological fluid through a molecular weight-based filter.

8. The method according to claim 1, wherein the IgG and the IgM are removed by incubating the biological fluid or separate sample derived from the biological fluid with polyethylene glycol.

9. The method according to claim 1, wherein the hepatocellular carcinoma is early stage hepatocellular carcinoma, alpha fetoprotein negative hepatocellular carcinoma, or early stage hepatocellular carcinoma that is also alpha fetoprotein negative hepatocellular carcinoma.

10. The method according to claim 2, wherein the function comprises respective optimized weighting coefficients for the determined age and gender, and for the measured amounts of the measured biomarkers.

11. The method according to claim 2, wherein the biomarkers are alphafetoprotein, fucosylated kininogen, alkaline phosphatase, and aspartate aminotransferase.

12. The method according to claim 2, wherein the biomarkers are alphafetoprotein, fucosylated kininogen, alkaline phosphatase, aspartate aminotransferase, and fucosylated alpha-1-antitrypsin.

13. The method according to claim 2, wherein the biomarkers are alphafetoprotein, fucosylated kininogen, alkaline phosphatase, aspartate aminotransferase, and fucosylated fetuin-A.

14. The method according to claim 2, wherein the hepatocellular carcinoma is early stage hepatocellular carcinoma, alpha fetoprotein negative hepatocellular carcinoma, or early stage hepatocellular carcinoma that is also alpha fetoprotein negative hepatocellular carcinoma.

15. The method according to claim 2, wherein the IgG is removed by incubating the biological fluid with Protein A/G, and the IgM is removed by passing the biological fluid through a molecular weight-based filter.

16. The method according to claim 2, wherein the IgG and the IgM are removed by incubating the biological fluid with polyethylene glycol.

* * * * *